United States Patent
Wang et al.

(10) Patent No.: US 12,383,418 B2
(45) Date of Patent: Aug. 12, 2025

(54) ANKLE JOINT DEVICE WITH A FOOT SUPPORT FEATURING ADJUSTABLE INITIAL ANGLE

(71) Applicant: SHANGHAI FOURIER INTELLIGENCE CO., LTD, Shanghai (CN)

(72) Inventors: Jun Wang, Jiangsu (CN); Tongchen Wang, Shanghai (CN); Danping Xiao, Jiangxi (CN); Jie Gu, Shanghai (CN); Chong Li, Shanghai (CN)

(73) Assignee: SHANGHAI FOURIER INTELLIGENCE CO., LTD, Shanghai (CN)

( * ) Notice: Subject to any disclaimer, the term of this patent is extended or adjusted under 35 U.S.C. 154(b) by 257 days.

(21) Appl. No.: 18/026,599

(22) PCT Filed: Aug. 5, 2021

(86) PCT No.: PCT/CN2021/110900
§ 371 (c)(1),
(2) Date: Mar. 16, 2023

(87) PCT Pub. No.: WO2022/062713
PCT Pub. Date: Mar. 31, 2022

(65) Prior Publication Data
US 2023/0329891 A1    Oct. 19, 2023

(30) Foreign Application Priority Data
Sep. 27, 2020   (CN) .......................... 202011029077.3

(51) Int. Cl.
*A61F 5/00* (2006.01)
*A61F 5/01* (2006.01)

(52) U.S. Cl.
CPC .... *A61F 5/0127* (2013.01); *A61F 2005/0167* (2013.01)

(58) Field of Classification Search
CPC .... A61F 5/0123; A61F 5/0125; A61F 5/0127; A61F 5/013; A61F 5/0195;
(Continued)

(56) References Cited

U.S. PATENT DOCUMENTS 4,738,252 A     4/1988  Friddle et al.
5,997,493 A  *  12/1999 Young ................... A61F 5/0125
                                                              602/5

(Continued)

FOREIGN PATENT DOCUMENTS

| CN | 111388282 | 7/2020 |
| CN | 109464264 | 9/2020 |
| CN | 111920655 | 3/2021 |

*Primary Examiner* — Adam Baker
(74) *Attorney, Agent, or Firm* — HAUPTMAN HAM, LLP (57) ABSTRACT

An ankle joint device comprises a base, an angle adjusting assembly, and a foot support member; the angle adjusting assembly comprises a rotation member and an anti-rotation member, wherein the rotation member is rotationally mounted on the base, and the anti-rotation member is slidably and detachably locked to the rotation member along the axial direction defined by the rotation member; the foot support member is mounted to the anti-rotation member, after the anti-rotation member slides away from the rotation member in the axial direction by a predetermined distance, the foot support member is allowed to rotate at a predetermined angle, and the foot support member is locked to the rotation member to rotate with the rotation member relative to the base after the anti-rotation member slides close to the rotation member in the axial direction by a predetermined distance in a state of being maintained at the predetermined angle.

4 Claims, 10 Drawing Sheets

(58) Field of Classification Search
CPC ...... A61F 2005/0158; A61F 2005/0165; A61F 2005/0167; A61F 2005/0169; A61F 2005/0179; A61F 2005/0197
USPC .......................................................... 602/16
See application file for complete search history.

(56) References Cited

U.S. PATENT DOCUMENTS

| | | | | |
|---|---|---|---|---|
| 6,648,843 | B1 * | 11/2003 | Marciano | A61F 5/0127 |
| | | | | 602/3 |
| 8,257,283 | B2 * | 9/2012 | Kaiser | A61H 1/0285 |
| | | | | 601/5 |
| 10,226,373 | B1 * | 3/2019 | McCoy | A61F 5/0125 |
| 2013/0053741 | A1 * | 2/2013 | Pittaccio | A61H 1/0277 |
| | | | | 403/113 |
| 2016/0374844 | A1 * | 12/2016 | DeHarde | F16F 15/04 |
| | | | | 602/16 |

* cited by examiner

ANKLE JOINT DEVICE WITH A FOOT SUPPORT FEATURING ADJUSTABLE INITIAL ANGLE

FIELD OF TECHNOLOGY

The present invention relates to an ankle joint mechanism, in particular to an ankle joint device with a foot support featuring adjustable initial angle.

BACKGROUND

Nowadays, medical devices are gradually used to assist users in rehabilitation training. As different parts of the human body have different bone structures, medical devices with different structures are needed to assist. The ankle joint is an important part of the human body, which directly determines whether people can walk normally.

For some users with damaged ankle joints, in order to prevent their damaged ankle joints from being damaged by walking before recovery, they usually need to wear an ankle joint mechanism. A patent application with the publication number CN110900569A discloses an ankle joint mechanism without a power source.

The ankle joint of the exoskeleton comprises the shank connecting rod, a heel block, a rotating shaft, an oil-free bushing, an end cap, a sole support, a flip connecting member, and a sole. This kind of ankle joint can only rotate, which can neither limit the range of ankle motion nor play a buffering role. However, different users have different ankle joint damage. Therefore, when training through the ankle joint of the exoskeleton, the training range is different. That is to say, since different users have different ankle joint damage, when they usually need plantarflexion and dorsiflexion, a starting angle between the foot support and the shank connecting member is correspondingly different. Otherwise, in the process of walking, it is easy to cause secondary damage due to the error of starting angle.

Further, in the patent with the publication number of CN110900569A, the range of motion of the ankle joint exoskeleton is not limited. In this way, it is easy to cause secondary damage to the ankle of some users whose ankle joints cannot be plantarflexed and dorsiflexed excessively because the range of motion of the ankle joint is not limited.

Further, a patent application with the publication number CN105616113A discloses a passive energy storage foot mechanism of an exoskeleton assisting lower limbs. The exoskeleton ankle joint has a limiting device and a passive energy storage mechanism including a spring, which can store and release energy to realize buffering, damping and automatic return when users walk. This kind of mechanism is small in size, simple in structure, and low in cost. However, when people walk, their ability to bear weight and support is poor. In an initial state of the ankle joint, a starting angle between the foot support and the shank connecting member is 90°, which is unadjustable. In addition, for users with weak leg muscle strength, the natural angle between plantar and shank is not 90°. In this case, if the user wears this rehabilitation device, it is prone to discomfort and ankle fatigue.

A patent application with the publication number of CN107042502A discloses "A CLOSED CHAIN CONNECTING ROD TYPE UNDERACTUATED LOWER EXTREMITY EXOSKELETON MECHANISM". The exoskeleton uses a single power source and a multi-linkage mechanism to connect and drive the hip joint, knee joint and ankle joint, thus reducing the overall weight of the exoskeleton. However, for users with different heights and body types, it is necessary to design different connecting rod lengths, which cannot solve the problems that the starting angle of the ankle joint cannot be adjusted and the range of ankle motion cannot be limited, so the applicable user scope is limited.

Further, generally, the foot support of the ankle joint mechanism needs to be rotationally mounted on a base, so that the foot support can freely rotate relative to the base with the plantarflexion or dorsiflexion of the user's foot when the user is using the ankle joint mechanism. In order to realize the adjustable initial angle of the foot support relative to the base, the angle of the foot support relative to the base needs to be adjusted and maintained in the corresponding adjusted state, and the foot support needs to be fixed in the adjusted state. This conflicts with the need for free rotation of the foot support relative to the base to some extent.

SUMMARY

Another purpose of the present invention is to provide an ankle joint device with a foot support featuring adjustable initial angle, wherein the initial angle between the foot support and the shank connecting member can be adjusted while being maintained in an adjusted state, and the foot support can be freely rotated.

A purpose of the present invention is to provide an ankle joint device with a foot support featuring adjustable initial angle, which can be applied to users with different ankle damage degrees.

Another purpose of the present invention is to provide an ankle joint device with a foot support featuring adjustable initial angle, when the foot support of the ankle joint device with a foot support featuring adjustable initial angle rotates relative to the shank connecting member, a rotation angle thereof can be limited to a predetermined range, thereby preventing the ankle joint of a user whose ankle joint cannot be excessively moved from secondary damage due to excessive rotation.

Another purpose of the present invention is to provide an ankle joint device with a foot support featuring adjustable initial angle, which can provide a buffering effect when a user walks, thereby preventing the ankle joint of the user from rotating rapidly and causing the secondary damage.

In order to realize at least one purpose of the present invention, the present invention provides an ankle joint device with a foot support featuring adjustable initial angle, which comprises:

a base;

an angle adjusting assembly, which comprises a rotation member and an anti-rotation member, wherein the rotation member is rotationally mounted on the base, wherein the anti-rotation member is slidably and detachably locked to the rotation member along the axial direction defined by the rotating shaft of the rotation member; and a foot support member, which is mounted to the anti-rotation member, after the anti-rotation member slides away from the rotation member in the axial direction by a predetermined distance, the foot support member is allowed to rotate at a predetermined angle as the anti-rotation member is separated from the rotation member, and the foot support member is locked to the rotation member to rotate with the rotation member relative to the base after the anti-rotation member slides close to the rotation member in the axial direction by a predetermined distance in a state of being maintained at the predetermined angle.

According to an embodiment of the present invention, the angle adjusting assembly includes an anti-rotation structure; the anti-rotation structure comprises a set of anti-rotation holes and a set of anti-rotation columns, which are respectively arranged on the circumference of the same diameter, wherein the anti-rotation hole is disposed on the rotation member, the anti-rotation column is disposed on the anti-rotation member, and the anti-rotation column is correspondingly inserted into the anti-rotation hole to lock the anti-rotation member to the rotation member.

According to an embodiment of the present invention, the angle adjusting assembly includes an anti-rotation structure, which comprises a set of anti-rotation holes and a set of anti-rotation columns, which are respectively arranged on the circumference of the same diameter, wherein the anti-rotation hole is disposed on the anti-rotation member, and the anti-rotation column is disposed on the rotation member and correspondingly inserted into the anti-rotation hole to lock the anti-rotation member to the rotation member.

According to an embodiment of the present invention, the foot support member is integrally formed toward one side of the rotation member to form the anti-rotation member.

According to an embodiment of the present invention, the angle adjusting assembly includes a mounting member, which is disposed between the rotation member and the anti-rotation member; the foot support member is fixed to the mounting member; at least a set of through holes is disposed on the mounting member, the through hole is arranged on the circumference having a diameter equal to that of the circumference where the anti-rotation hole or the anti-rotation column is; the anti-rotation column is inserted into the anti-rotation hole through the through hole on the mounting member, and the anti-rotation column slides away from the anti-rotation hole after the anti-rotation member slides away from the rotation member along the axial direction for a predetermined distance.

According to an embodiment of the present invention, a perforation is formed in the middle part of the base, a shaft hole is formed in the middle part of the rotation member, and the middle part of the anti-rotation member extends toward the base along the axial direction to form an extension shaft, which passes through the shaft hole and the perforation successively to form an end portion.

According to an embodiment of the present invention, the ankle joint device with a foot support featuring adjustable initial angle includes an elastic member, which is connected to the anti-rotation member in such a manner that the anti-rotation member tends to move in the axial direction toward the rotation member.

According to an embodiment of the present invention, the elastic member is disposed between the anti-rotation member and the mounting member in a compressed manner.

According to an embodiment of the present invention, the angle adjusting assembly includes at least an angle limiting structure, which comprises at least a limiting pin and an arc-shaped limiting groove, one side of the rotation member facing the base extending toward the base to form the limiting pin, the arc-shaped limiting groove being disposed on the base facing the side of the rotation member, and the limiting pin being inserted into the arc-shaped limiting groove.

According to an embodiment of the present invention, the angle adjusting assembly includes at least an angle limiting structure, which comprises at least a limiting pin and an arc-shaped limiting groove, one side of the base extending toward the rotation member to form the limiting pin, the arc-shaped limiting groove being disposed at the side of the rotation member facing the base, and the limiting pin being inserted into the arc-shaped limiting groove.

According to an embodiment of the present invention, the angle adjusting assembly includes at least an angle limiting structure, which comprises at least a limiting pin and an arc-shaped limiting groove, one side of the mounting member facing the base extending toward the base to form the limiting pin, the arc-shaped limiting groove being disposed on the side of the base facing the rotation member, and the limiting pin extending into the arc-shaped limiting groove over the rotation member.

According to an embodiment of the present invention, the central angle of the circumference formed by the arc-shaped limiting groove of the angle limiting structure minus the central angle of the arc-shaped limiting groove occupied by the limiting pin is implemented as 60°-80°.

According to an embodiment of the present invention, the ankle joint device with a foot support featuring adjustable initial angle includes a buffering assembly, which is disposed between the base and the rotation member in such a manner that when the rotation member is rotated relative to the base and deviates from the set initial angle, the buffering assembly maintains a restoring force applied to the rotation member before returning to rotating.

Further purposes and advantages of the present invention will be fully embodied by understanding the following description.

These and other purposes, features and advantages of the present invention are fully embodied in the following detailed description.

DETAILED DESCRIPTION OF THE EMBODIMENTS

The preferred embodiments in the following description are by way of example only and other obvious variations are conceivable to those skilled in the art. The basic principles of the present invention as defined in the following description may be applied to other embodiments, variations, modifications, equivalents, and other technical solutions that do not depart from the essence and scope of the present invention.

As will be appreciated by those skilled in that art, in the disclosure of the present invention, the terms "longitudinal", "transverse", "up", "down", "front", "back", "left", "right", "vertical", "horizontal", "top", "bottom", "inside", "outside" and the like indicate an orientation or positional relationship based on the orientation or positional relationship shown in the drawings, they are intended only for the convenience of describing the present invention and simplifying the description, and are not intended to indicate or imply that the devices or elements referred to must have a particular orientation, be constructed and operate in a particular orientation. Therefore, the terms described above cannot be construed as limit to the present invention.

Combining with FIGS. 1 to 8, an ankle joint device with a foot support featuring adjustable initial angle according to a preferred embodiment of the present invention will be described in detail below, wherein the ankle joint device with a foot support featuring adjustable initial angle is suitable for providing rehabilitation training for a user with ankle joint damage, thereby limiting a rotation angle of the ankle joint of the user while ensuring that no secondary damage is caused to the ankle joint of the user.

Specifically, the ankle joint device with a foot support featuring adjustable initial angle comprises a foot support member 10, an angle adjusting assembly 20 and a base 30. The foot support member 10 is rotationally mounted on the base 30 so that when the user uses the ankle joint device with a foot support featuring adjustable initial angle, the foot support member 10 can be rotated together with the foot of the user as the foot is plantarflexed or dorsiflexed.

The angle adjusting assembly 20 is disposed between the foot support member 10 and the base 30 to adjust and maintain an initial angle formed between the foot support member 10 and the base 30.

Figure 1:
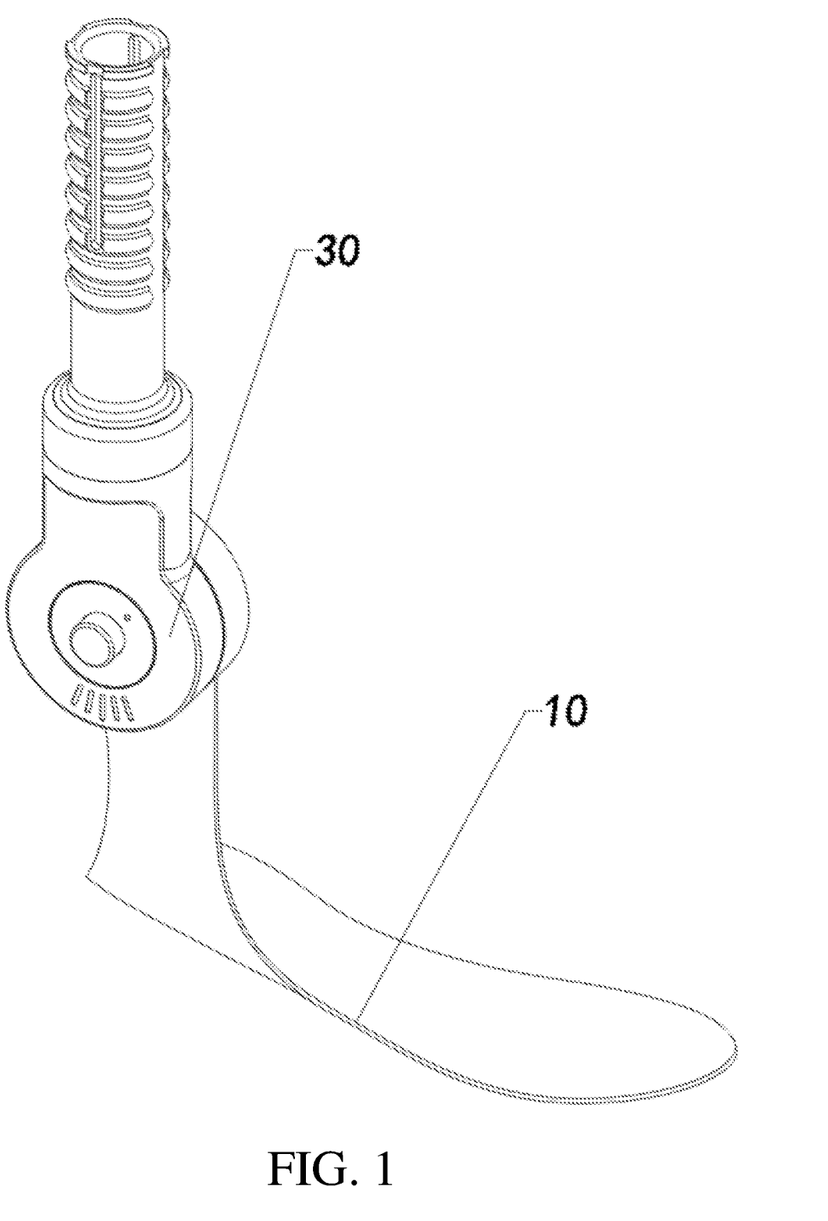
FIG. 1 shows a perspective view of an ankle joint device with a foot support featuring adjustable initial angle of the present invention.
Figure 2A:
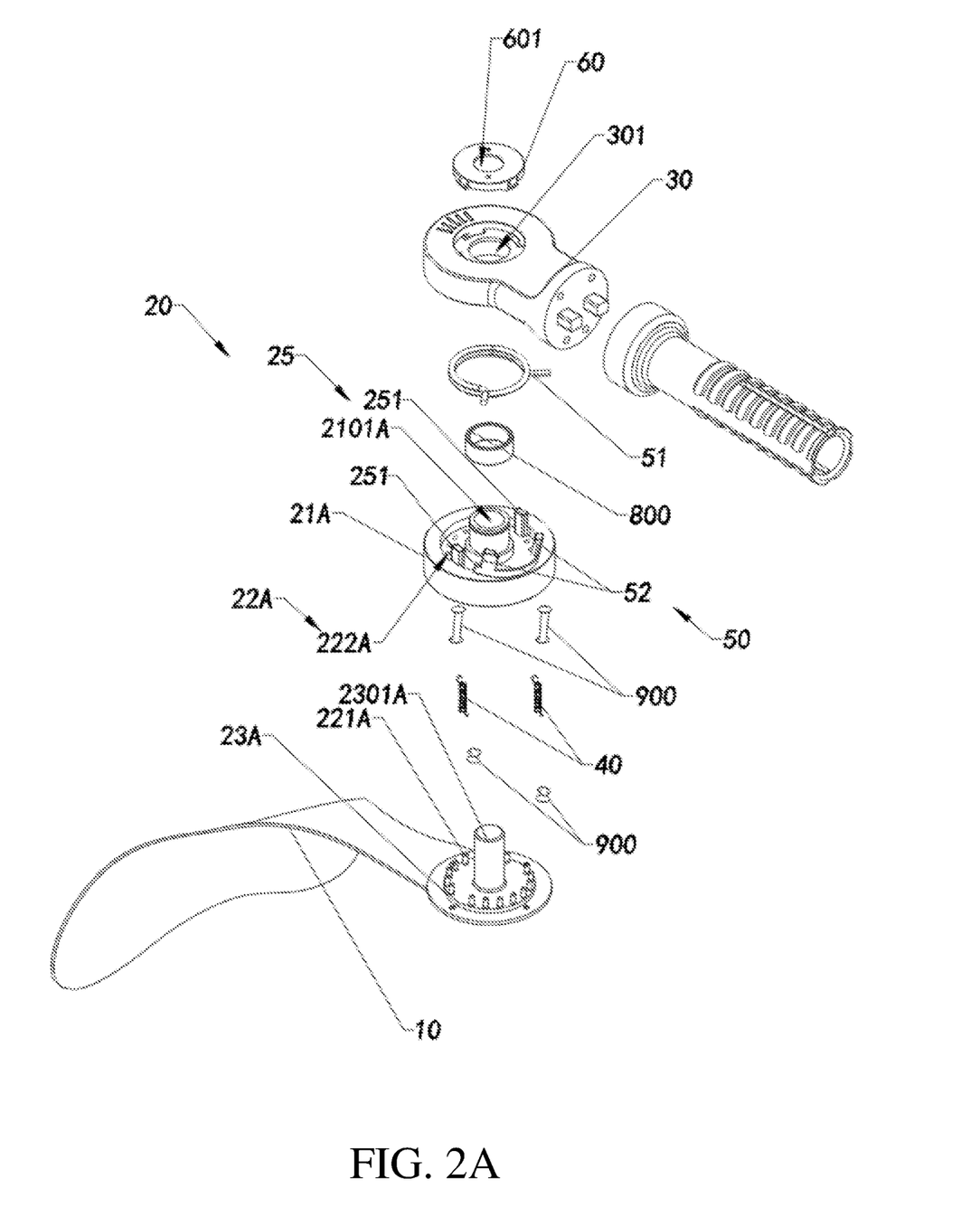
FIGS. 2A and 2B respectively show exploded views at different angles of the ankle joint device with a foot support featuring adjustable initial angle of an embodiment of the present invention.
Figure 2B:
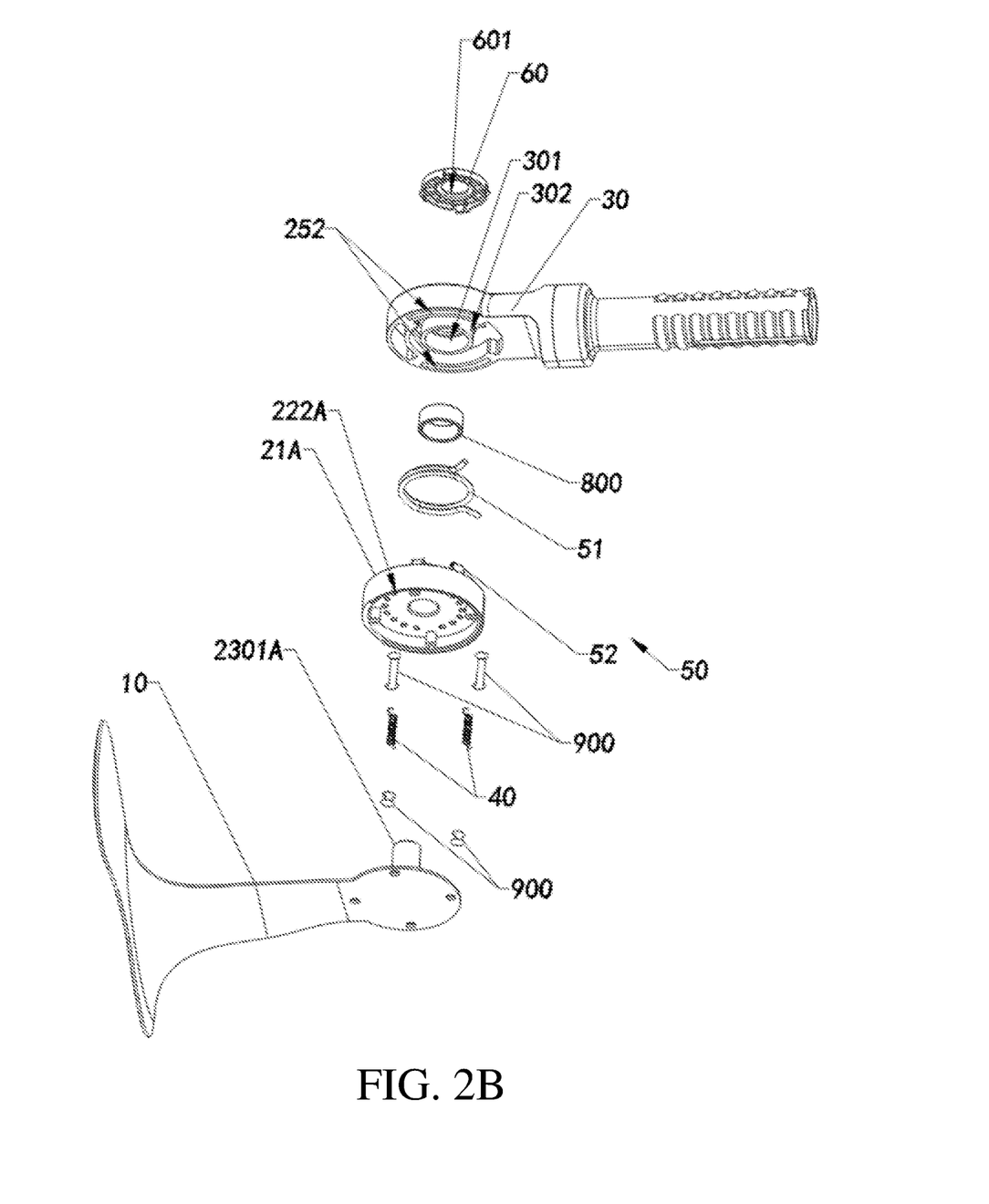

Referring to FIGS. 1, 2A, and 2B, in an embodiment, the angle adjusting assembly 20 comprises a rotation member 21A, an anti-rotation structure 22A, and an anti-rotation member 23A. The anti-rotation member 23A is slidably and detachably locked to the rotation member 21A along the axial direction defined by the rotating shaft of the rotation member 21A. The anti-rotation member 23A is formed integrally extending from the foot support member 10 toward one side of the rotation member 21A. The anti-rotation member 23A on the foot support member 10 is rotatably and lockably mounted to the rotation member 21A through the anti-rotation member 22A. The rotation member 21A is rotatably mounted on the base 30 so that the foot support member 10 can rotate relative to the base 30.

Thus, when it is necessary to adjust the initial angle formed between the foot support member 10 and the base 30, the foot support member 10 is rotated relative to the rotation member 21A, and the foot support member 10 is maintained in the rotated position by the anti-rotation structure 22A so that the initial angle between the foot support member 10 and the base 30 is adjusted.

The anti-rotation structure 22A includes a set of anti-rotation columns 221A and a set of anti-rotation holes 222A, which are respectively arranged on the circumference of the same diameter size.

In an embodiment, the anti-rotation columns 221A are provided on one side of the anti-rotation member 23A of the foot support member 10 facing the rotation member 21A, and the anti-rotation columns 221A extend in the axial direction of the rotating shaft of the anti-rotation member 23A. The anti-rotation holes 222A are disposed on the rotation member 21A, and the anti-rotation holes 222A are provided in alignment with the anti-rotation columns 221A so that when the anti-rotation member 23A moves toward the base 30 in the axial direction of the rotating shaft of the foot support member 10, the anti-rotation columns 221A are inserted into the anti-rotation holes 222A, so that the anti-rotation member 23A is fixed relative to the rotation member 21A, and the foot support member 10 is maintained in the corresponding state.

In a modified embodiment of the present embodiment, the anti-rotation columns 221A are disposed on one side of the rotation member 21A facing the foot support member 10. The anti-rotation holes 222A are disposed in the anti-rotation member 23A of the foot support member 10.

In any of the above embodiments, when it is necessary to adjust the initial angle of the foot support member 10 relative to the base 30, it only needs to move the anti-rotation member 23A in a direction away from the base 30 in the axial direction of the rotating shaft of the foot support member 10, so that the anti-rotation columns 221A of the anti-rotation structure 22A slide away from the anti-rotation holes 222A, thereby enabling the foot support member 10 to be rotated relative to the rotation member 21A. After the foot support member 10 is rotated by a predetermined angle relative to the rotation member 21A, the anti-rotation member 23A is moved in a direction close to the base 30 in the axial direction of the rotating shaft of the anti-rotation member 23A, so that the anti-rotation columns 221A are reinserted into the anti-rotation holes 222A, and the foot support member 10 is fixed in the adjusted state by the anti-rotation member 22A.

In this embodiment, a perforation 301 is formed in the middle part of the base 30. A shaft hole 2101A is formed in the middle part of the rotation member 21A. The middle part of the anti-rotation member 23A extends toward the base 30 in the axial direction of the rotating shaft of the foot support member 10 to form an extension shaft 2301A, which passes through the shaft hole 2101A and the perforation hole 301 successively to form an end portion, so as to allow a user to slide and rotate the foot support member 10 in the axial direction of the rotating shaft of the foot support member 10 by manually locking the end portion of the extension shaft 2301A.

Figure 3A:
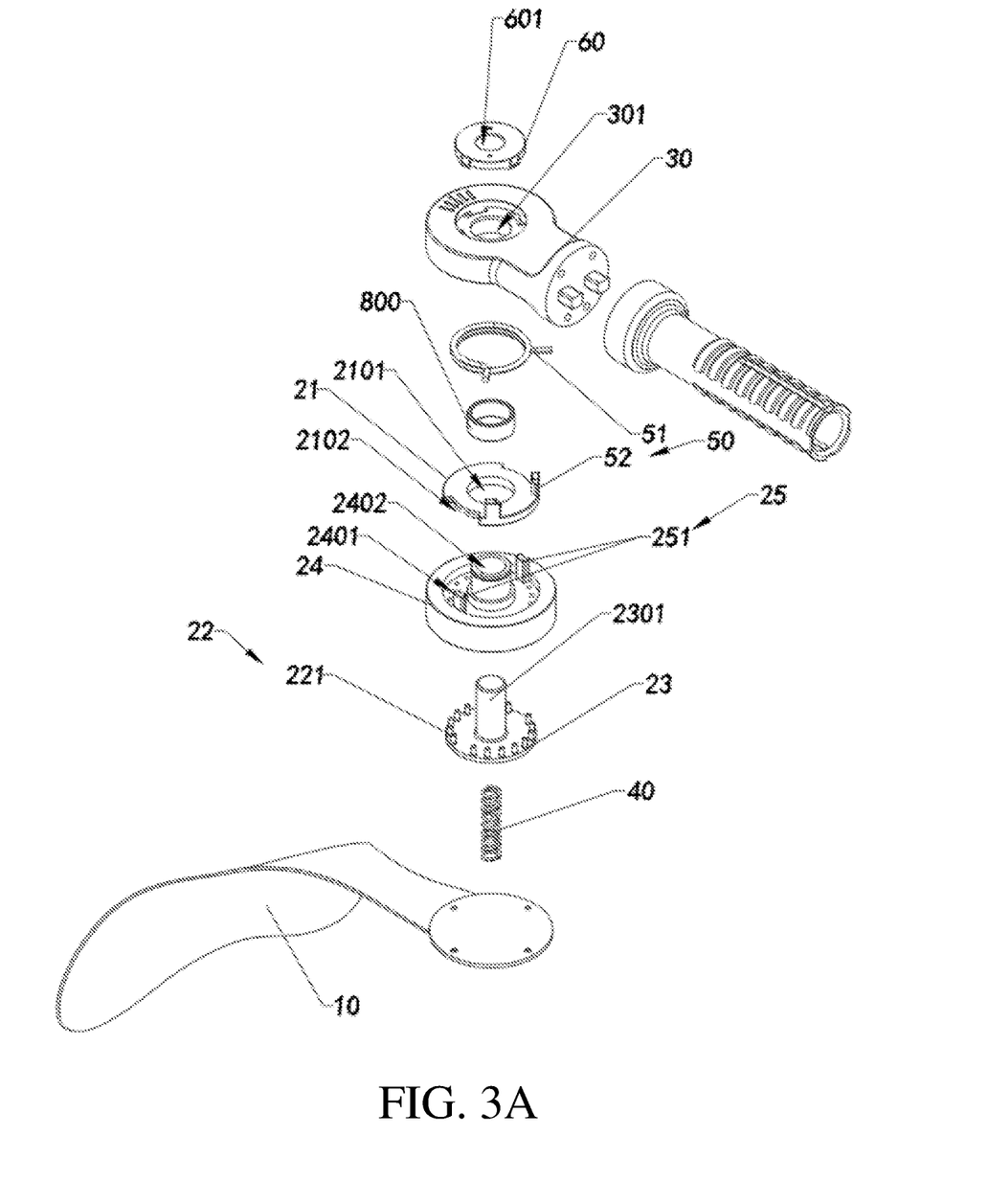
FIGS. 3A and 3B respectively show exploded views at different angles of the ankle joint device with a foot support featuring adjustable initial angle of another embodiment of the present invention.
Figure 3B:
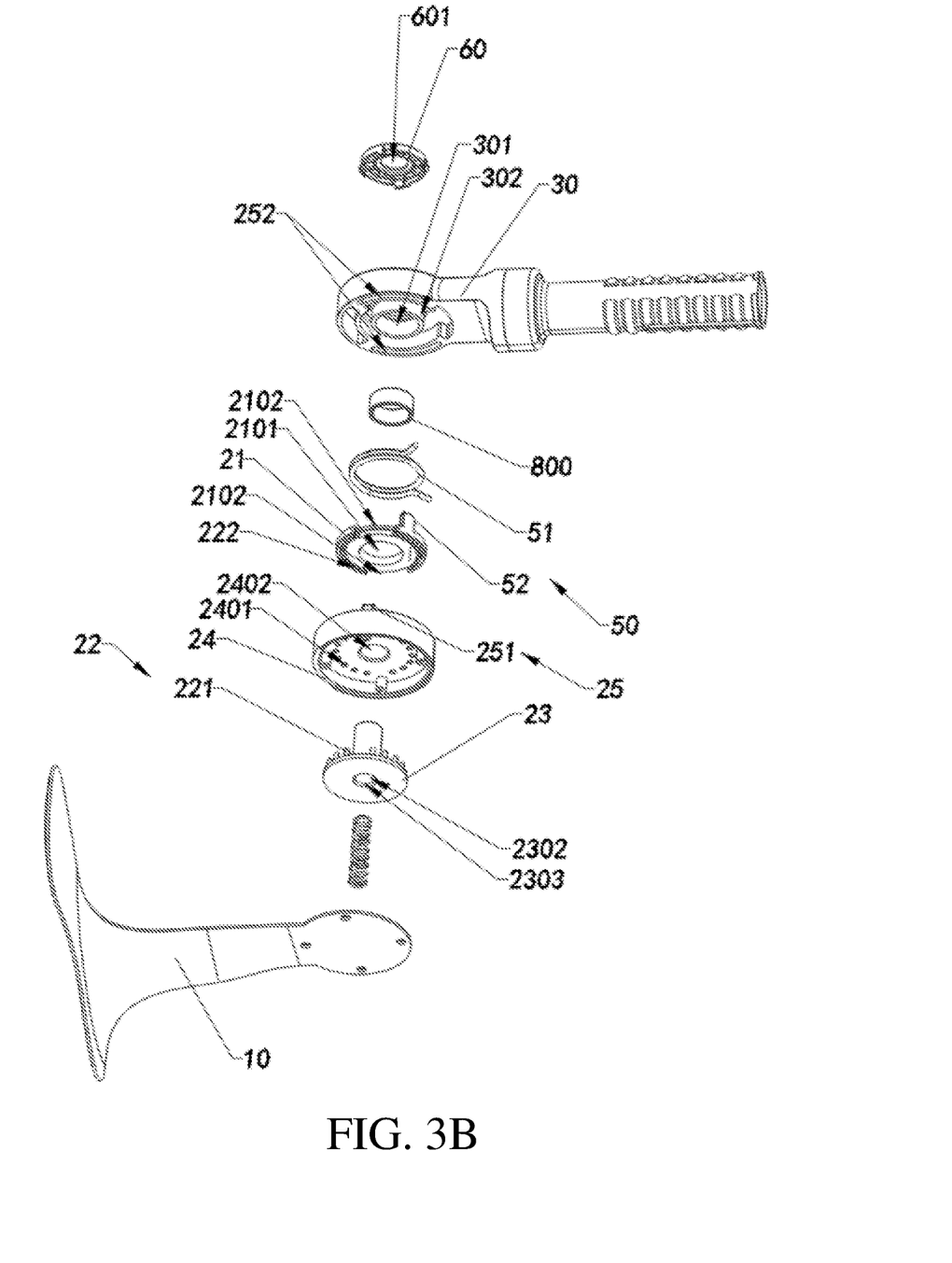
Figure 4:
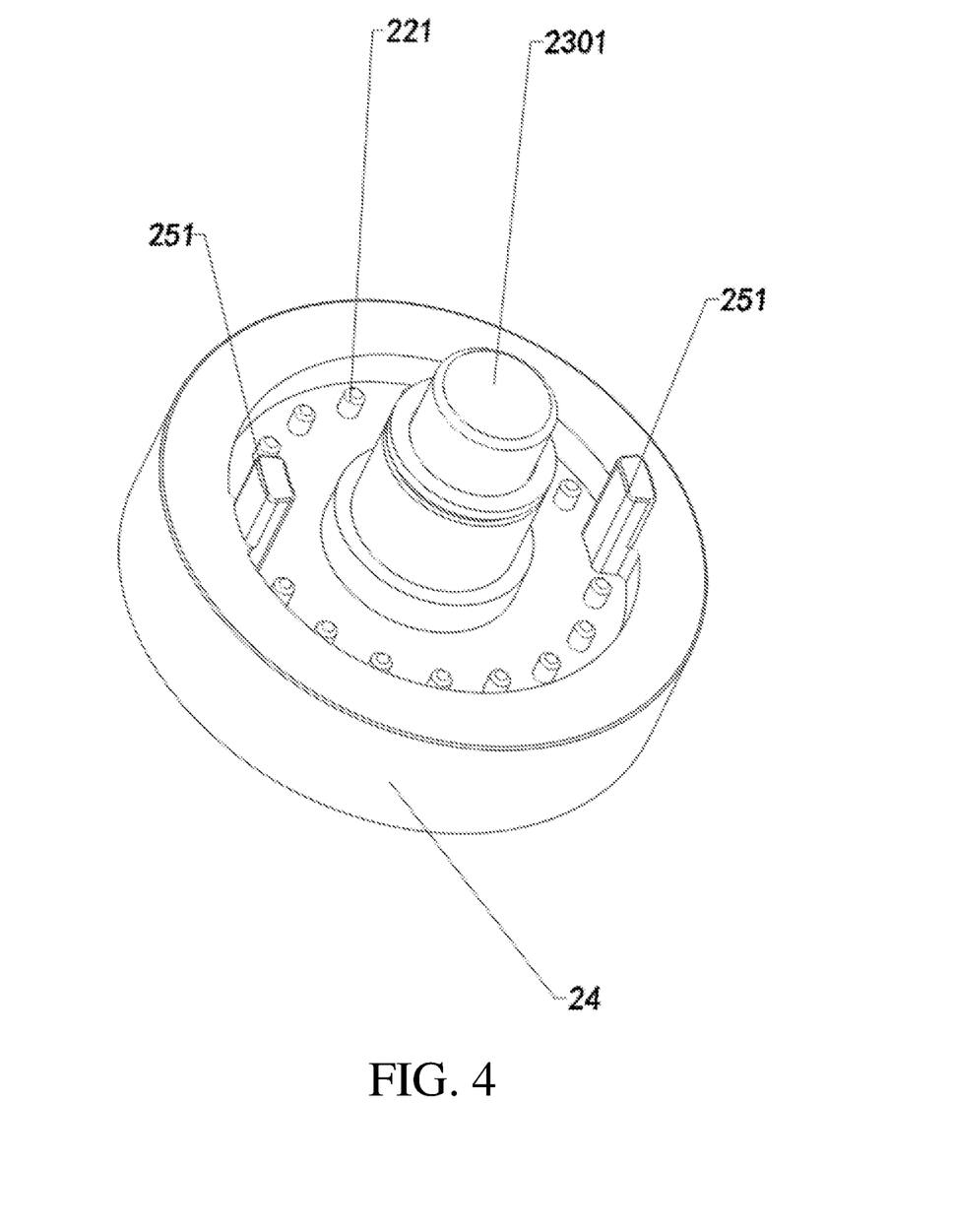
FIG. 4 shows an assembly view of a portion of the structure of the ankle joint device with a foot support featuring adjustable initial angle of the second embodiment of the present invention.

Referring to FIGS. 1, 3A, and 3B, in another embodiment, the angle adjusting assembly 20 comprises a rotation member 21, an anti-rotation structure 22, and an anti-rotation member 23. The anti-rotation member 23 is slidably and detachably locked to the rotation member 21 along the axial direction defined by the rotating shaft of the rotation member 21.

The anti-rotation structure 22 includes a set of anti-rotation columns 221 and a set of anti-rotation holes 222, which are respectively arranged on the circumference of the same diameter size.

In this embodiment, the anti-rotation columns 221 are provided on one side of the anti-rotation member 23 of the foot support member 10 facing the rotation member 21, and the anti-rotation columns 221 extend in the axial direction of the rotating shaft of the anti-rotation member 23. The anti-rotation holes 222 are disposed on the rotation member 21 and provided in alignment with the anti-rotation columns 221 so that when the anti-rotation member 23 moves toward the base 30 in the axial direction of the rotating shaft of the foot support member 10, the anti-rotation columns 221 are inserted into the anti-rotation holes 222, so that the anti-rotation member 23 is fixed relative to the rotation member 21, and the foot support member 10 is maintained in the corresponding state.

Also, as a modified embodiment, the anti-rotation columns 221 are disposed on one side of the rotation member 21 facing the foot support member 10. The anti-rotation holes 222 are disposed in the anti-rotation member 23A of the foot support member 10. In order to enable those skilled in the art to understand the present invention, at least an embodiment and the accompanying drawings of the present invention are set forth only by the example that the anti-rotation columns 221 are disposed on the side of the anti-rotation member 23 of the foot support member 10 facing the rotation member 21, and the anti-rotation holes 222 are disposed on the rotation member 21.

The angle adjusting assembly 20 includes a mounting member 24, which is provided between the rotation member 21 and the anti-rotation member 23. The foot support member 10 is fixed to the mounting member 24. The anti-rotation member 23 is axially movable between the rotation member 21 and the foot support member 10.

The mounting member 24 is provided with at least a set of through holes 2401, which are arranged on the circumference equal in diameter to the circumference of the anti-rotation holes 222 or the anti-rotation columns 221. The anti-rotation columns 221 are inserted into the anti-rotation holes 222 through the through hole 2401 in the mounting member 24 to lock the anti-rotation member 23 and the mounting member 24 to the rotation member 21.

In an embodiment, after the anti-rotation member 23 slides away from the rotation member 21 in the axial direction by a predetermined distance, the anti-rotation columns 221 slide away from the anti-rotation holes 222, so that when the anti-rotation member 23 is subsequently rotated, the mounting member 24 is driven to rotate the predetermined angle together so that the foot support member 10 mounted on the mounting member 24 can be adjusted to the predetermined angle with the mounting member 24.

Preferably, in an embodiment, after the anti-rotation member 23 slides axially away from the rotation member 21 by a predetermined distance, the anti-rotation columns 221 slide away from the anti-rotation holes 222 and are maintained in the through hole 2401.

A perforation 301 is formed in the middle part of the base 30. A shaft hole 2101 is formed in the middle part of the rotation member 21. The middle part of the anti-rotation member 23 extends toward the base 30 in the axial direction of the rotating shaft of the foot support member 10 to form an extension shaft 2301, which passes through the shaft hole 2101 and the perforation hole 301 successively to form an end portion, so as to allow a user to slide and rotate the foot support member 10 in the axial direction of the rotating shaft of the foot support member 10 by manually locking the end portion of the extension shaft 2301.

In another embodiment, the middle part of the mounting member 24 is formed with a mounting hole 2402 for the extension shaft 2301 to pass through.

The ankle joint device with a foot support featuring adjustable initial angle includes an elastic member 40, which is connected to the anti-rotation member 23 in such a manner that the anti-rotation member 23 tends to move in the axial direction toward the rotation member 21.

Preferably, the ankle joint device with a foot support featuring adjustable initial angle further includes a sliding bearing 800, which is sleeved on the perforation 301 of the base 30, and when the extension shaft 2301 passes through the perforation 301 of the base 30, the sliding bearing 800 is maintained between the extension shaft 2301 and the perforation 301 of the base 30, to reduce friction between the extension shaft 2301 and the base 30.

In an embodiment shown in FIGS. 2A and 2B, the elastic member 40 is maintained between the rotation member 21A and the anti-rotation member 23A in a stretched manner. Preferably, the elastic member 40 is implemented as a hook spring. One end of the elastic member 40 is hooked to the rotation member 21A, and the other end of the elastic member 40 is hooked to the anti-rotation member 23A. More notably, both ends of the elastic member 40 are hooked to one end of a pin 900, respectively, wherein the pin 900 fixed to the rotation member 21A is rotatable relative to the rotation member 21A, and the pin 900 fixed to the anti-rotation member 23A is rotatable relative to the anti-rotation member 23A. It will be appreciated that the pin 900 may be provided with a hole to hook the elastic member 40.

Figure 5:
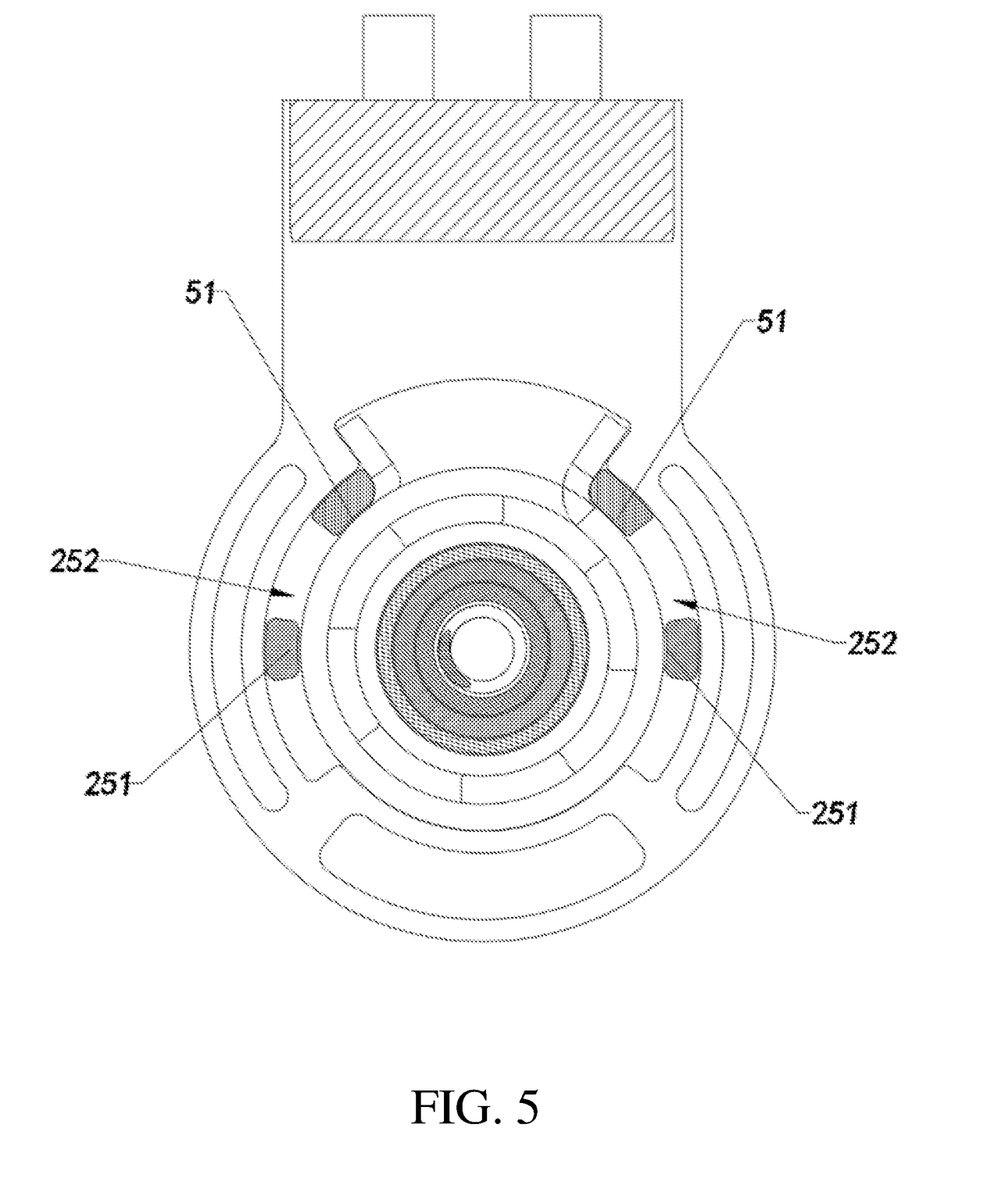
FIG. 5 shows a cross-sectional view of one angle of the ankle joint device with a foot support featuring adjustable initial angle of the present invention.
Figure 6:
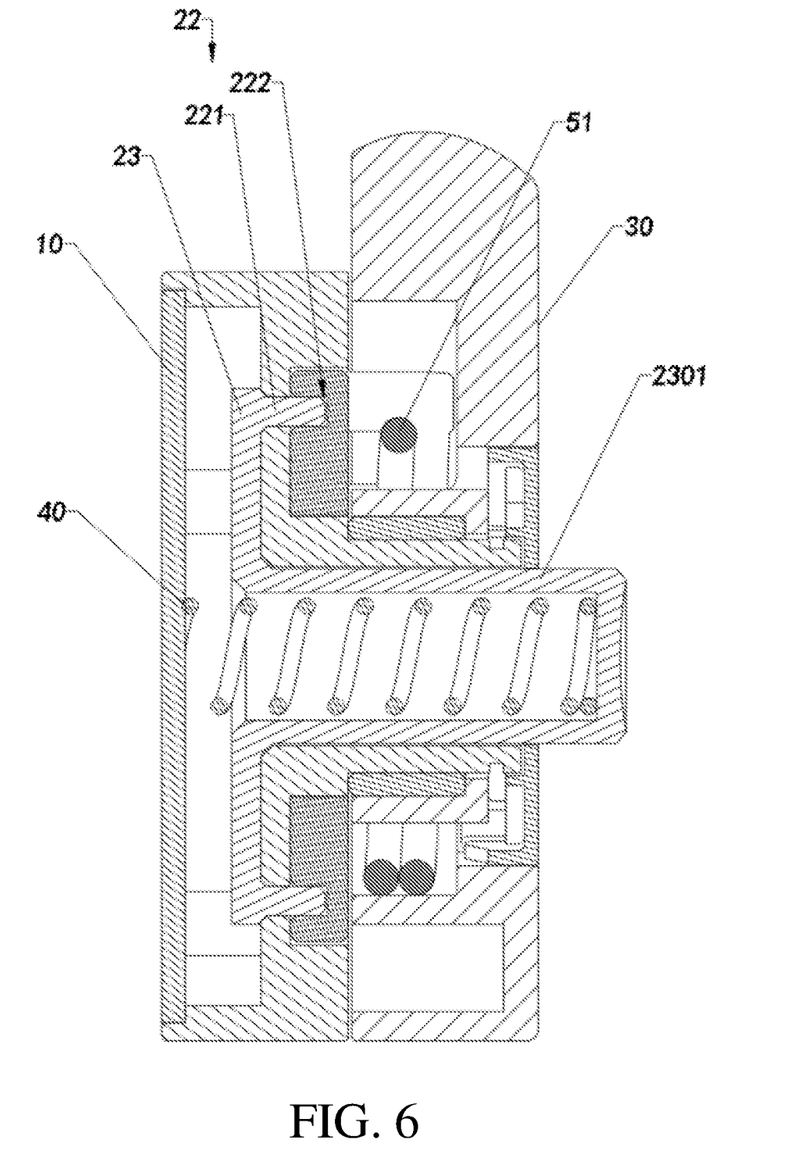
FIG. 6 shows a cross-sectional view of one angle of the ankle joint device with a foot support featuring adjustable initial angle of the second embodiment of the present invention.

In an embodiment, the elastic member 40 is disposed between the anti-rotation member 23 and the foot support member 10 in a compressed manner. Preferably, the extension shaft 2301 of the anti-rotation member 23 forms a mounting cavity 2302 and a mounting opening 2303 communicating with the mounting cavity 2302. After the foot support member 10 is mounted and fixed to the mounting member 24 from the mounting opening 2303, the elastic member 40 is accommodated in the mounting cavity 2302 in a compressed manner.

Further, the angle adjusting assembly 20 also includes at least an angle limiting structure 25, which is disposed between the rotation member 21 and the base 30, to limit an angle at which the rotation member 21 rotates relative to the base 30.

Specifically, the angle limiting structure 25 includes at least a limiting pin 251 and an arc-shaped limiting groove 252. The limiting pin 251 is inserted into the arc-shaped limiting groove 252.

In an embodiment, the side of the rotation member 21 facing the base 30 extends toward the base 30 to form the limiting pin 251. The arc-shaped limiting groove 252 is disposed on the side of the base 30 facing the rotation member 21.

In a modified embodiment of the present embodiment, the side of the base 30 facing the base 30 extends toward the rotation member 21 to form the limiting pin 251, and the arc-shaped limiting groove 252 is disposed on the side of the rotation member 21 facing the base 30.

In another embodiment, the side of the mounting member 24 facing the base 30 extends toward the base 30 to form the limiting pin 251. The arc-shaped limiting groove 252 is disposed on the side of the base 30 facing the rotation member 21. Accordingly, the limiting pin 251 extends beyond the rotation member 21 into the arc-shaped limiting groove 252.

In a modified embodiment of the present embodiment, the side of the base 30 facing the rotation member 21 extends toward the rotation member 21 to form the limiting pin 251, and the arc-shaped limiting groove 252 is disposed on the side of the rotation member 21 facing the base 30.

Preferably, in the present embodiment, an arc-shaped avoidance opening 2102 is formed on a circumference of the rotation member 21, and the limiting pin 251 is inserted into the arc-shaped limiting groove 252 through the arc-shaped avoidance opening 2102. With this arrangement, when the angle adjusting assembly 20 and the foot support member 10 are rotated together relative to the base 30, the limiting pin 251 is not blocked by the rotation member 21 and cannot be rotated.

Due to the design of the arc-shaped limiting groove 252, when the foot support member 10 rotates with the rotation member 21 relative to the base 10, the rotation angle of the foot support member 10 and the angle adjusting assembly 20 relative to the base 30 will be limited.

Preferably, the angle adjusting assembly 20 includes at least two angle limiting structures 25, and the limiting pins 251 in the angle limit structures 25 are symmetrically disposed on one circumference.

Preferably, the central angle of the circumference formed by the arc-shaped limiting groove 252 of the angle limiting structures 25 minus the central angle of the arc-shaped limiting groove 252 occupied by the limiting pin 251 is implemented as 60°-80°, which allows the foot support member 10 to rotate at an ergonomic angle.

Further, the ankle joint device with a foot support featuring adjustable initial angle also includes a buffering assembly 50, which is disposed between the base 30 and the rotation member 21. When the rotation member 21 is rotated relative to the base 30 and deviates from the set initial angle, the buffering assembly 50 maintains a restoring force applied to the rotation member 21 at all times, so that the foot support member 10 tends to return to the set initial angle and maintains balance.

Understandably, when a user uses the ankle joint device with a foot support featuring adjustable initial angle, the foot of the user is supported on the foot support member 10, and when the user's foot is plantarflexed or dorsiflexed, the rotation member 21 on which the foot support member 10 is mounted is rotated relative to the base 30 and deviates from the initial angle. Accordingly, the buffering assembly 50 will generate a predetermined amount of restoring force, thereby reducing the amount of rotation of the foot of the user with the foot support member 10 per unit time, and thus avoiding the aggravation of damage caused by rapid rotation of the ankle of the user. In other words, the buffering assembly 50 is capable of playing a predetermined buffering role.

Further, since the angle limiting structure 25 is provided, the angle at which the rotation member 21 rotates with the foot support member 10 relative to the base 30 can be limited to a predetermined range, thereby preventing a user's foot damage from aggravating due to excessive rotation of the foot support member 21.

Figure 7:
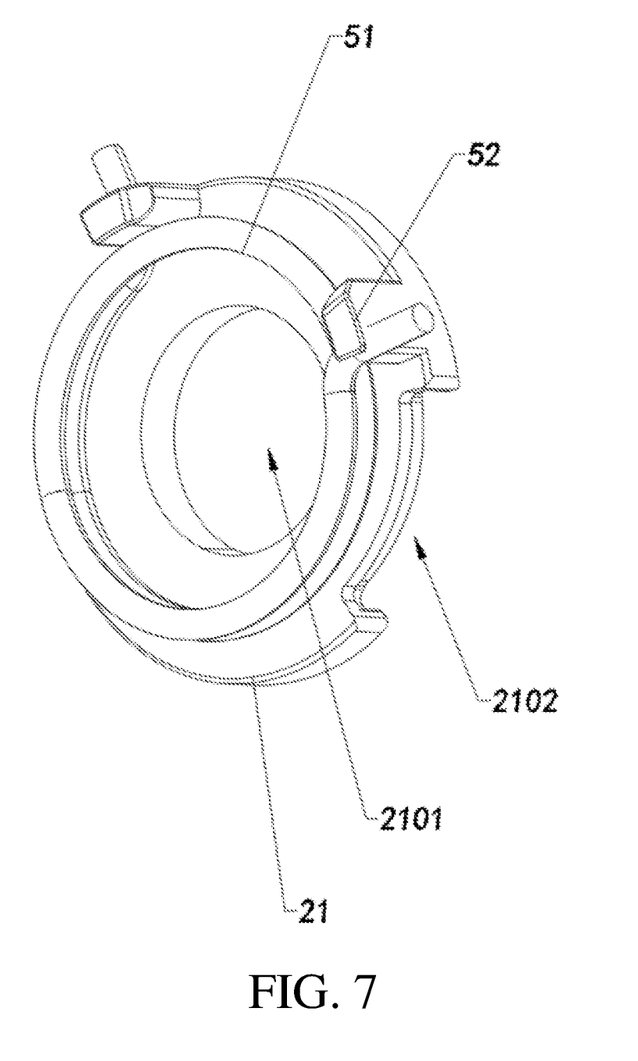
FIG. 7 shows an assembly view between a rotation member and a torsion spring in the ankle joint device with a foot support featuring adjustable initial angle of the second embodiment of the present invention.
Figure 8:
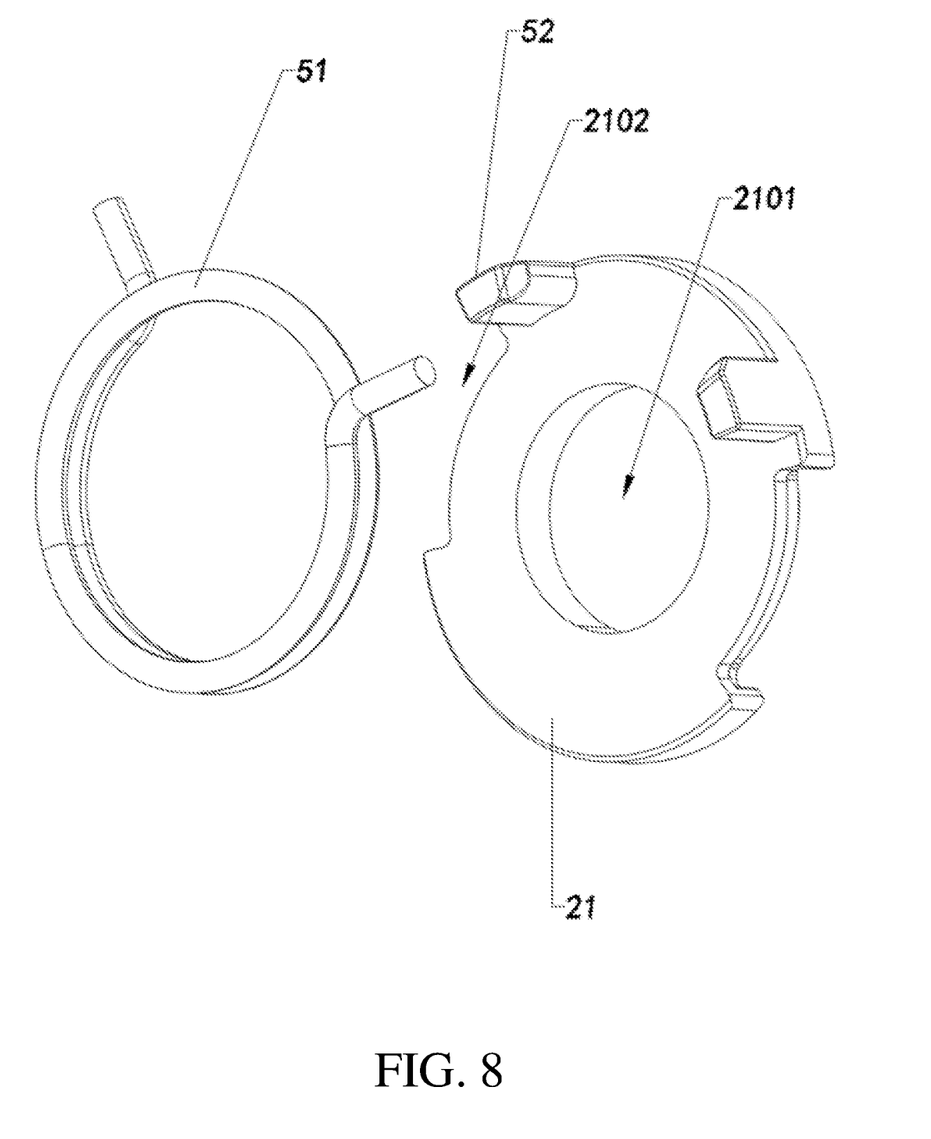
FIG. 8 shows an exploded view between the rotation member and the torsion spring in the ankle joint device with a foot support featuring adjustable initial angle of the second embodiment of the present invention.

Specifically, the buffering assembly 50 includes a torsion spring 51 and at least a pair of force-applying arms 52.

The torsion spring 51 is disposed between the base 30 and the rotation member 21, and when the rotation member 21 rotates relative to the base 30, the torsion spring 51 is forced to the force-applying arm 52 in a radially expandable manner.

In an embodiment, the rotation member 21 extends toward the base 30 to form a bump, which is defined as the force-applying arm 52. Both ends of the torsion spring 51 are fixed respectively. The torsion spring 51 is mounted on the force-applying arm 52, the diameter of the circumference of the force-applying arm 52 is larger than the cross-sectional diameter of the torsion spring 51 in the state of no force, so as to form an expansion space of a predetermined size between the torsion spring 51 and the side wall of the force-applying arm 52, thereby allowing the torsion spring 51 to expand in an annular mounting groove 302 provided on the base 30 after being pressed by the force-applying arm 52.

In a modified embodiment of the present embodiment, the base 30 extends toward the rotation member rotor 21 to form the bump, which is defined as the force-applying arm 52. Both ends of the torsion spring 51 are fixed respectively. The torsion spring 51 is mounted on the force-applying arm 52, the diameter of the circumference of the force-applying arm 52 is larger than the cross-sectional diameter of the torsion spring 51 in the state of no force, so as to form an expansion space of a predetermined size between the torsion spring 51 and the side wall of the force-applying arm 52, thereby allowing the torsion spring 51 to expand in an annular mounting groove 302 after being pressed by the force-applying arm 52.

Further, the ankle joint device with a foot support featuring adjustable initial angle includes an end cap 60, and an end hole 601 is provided in the middle part of the end cap 60 for the extension shaft 2301 to pass through. The end cap 60 covers the perforation 301 of the base 30.

It will be understood by those skilled in the art that the embodiments of the present invention shown in the above description are by way of example only, and the present invention is not limited thereto. The purpose of the present invention has been fully and effectively achieved. The functional and structural principles of the present invention have been shown and explained in the embodiments, and any variations or modifications may be made to the embodiments of the present invention without departing from the principles.

What is claimed is:

1. An ankle joint device with a foot support featuring an adjustable initial angle, characterized in comprising:

a base;

an angle adjusting assembly, which comprises a rotation member, an anti-rotation structure, a mounting member, an angle limiting structure and an anti-rotation member; wherein the rotation member is rotationally mounted on the base; wherein the anti-rotation member is slidably and detachably locked to the rotation member along an axial direction defined by a rotating shaft of the rotation member; wherein the anti-rotation structure comprises a set of anti-rotation holes and a set of anti-rotation columns, which are respectively arranged on a circumference of the same diameter, wherein the set of anti-rotation holes is disposed on the rotation member, wherein the set of anti-rotation columns is disposed on the anti-rotation member, wherein the set of anti-rotation columns is correspondingly inserted into the set of anti-rotation holes to lock the anti-rotation member to the rotation member, wherein the mounting member is disposed between the rotation member and the anti-rotation member, wherein at least a set of through holes is disposed on the mounting member, which the set of through holes is arranged on the circumference having a diameter equal to that of the circumference where the set of anti-rotation holes or the set of anti-rotation columns, wherein the set of anti-rotation columns is inserted into the anti-rotation hole through the set of through holes on the mounting member; wherein after the anti-rotation member slides away from the rotation member along the axial direction for a predetermined distance, the set of anti-rotation columns slides away from the set of anti-rotation holes while staying in the set of through holes; wherein the angle adjusting assembly comprises at least a limiting pin and at least an arc-shaped limiting groove, wherein one side of the mounting member facing the base extends toward the base to form the limiting pin; wherein the rotation member is provided with an arc-shaped avoidance opening, the arc-shaped limiting groove is disposed on the side of the base facing the rotation member, and the limiting pin is inserted into the arc-shaped avoidance opening after passing through the arc-shaped avoidance opening;

a buffering assembly, which comprises a torsion spring and at least a pair of force-applying arms; wherein the rotation member extends toward the base to form a bump, which is defined as the pair of force-applying arms; wherein the torsion spring is disposed between the base and the rotation member, and the torsion spring is disposed to the pair of force-applying arms and both end portions thereof are fixed; wherein when the rotation member rotates relative to the base, the torsion spring is compressed by the pair of force-applying arms and then expands in an annular mounting groove disposed on the base, so that when the rotation member rotates relative to the base and deviates from the set initial angle, the torsion spring maintains a restoring force applied to the rotation member to a state before rotation;

a foot support member, which is fixed to the mounting member, so that after the anti-rotation member slides away from the rotation member in the axial direction by a predetermined distance, the anti-rotation member slides away from the set of anti-rotation holes, wherein the foot support member is allowed to rotate at a predetermined angle as the anti-rotation member is separated from the rotation member, and the foot support member is locked to the rotation member to rotate with the rotation member relative to the base after the anti-rotation member slides close to the rotation member in the axial direction by a predetermined distance in a state of being maintained at the predetermined angle; and an elastic member, which is disposed between the anti-rotation member and the mounting member in such a manner that the elastic member is compressed.

2. The ankle joint device with a foot support featuring an adjustable initial angle of claim 1, characterized in that a perforation is formed in a middle part of the base, a shaft hole is formed in a middle part of the rotation member, and a middle part of the anti-rotation member extends toward the base along the axial direction to form an extension shaft, which passes through the shaft hole and the perforation successively to form an end portion.

3. The ankle joint device with a foot support featuring an adjustable initial angle of claim 1, characterized in that the central angle of the circumference formed by the arc-shaped limiting groove of the angle limiting structure minus the central angle of the arc-shaped limiting groove occupied by the limiting pin is implemented as 60°-80°.

4. The ankle joint device with a foot support featuring an adjustable initial angle of claim 1, characterized in that the angle adjusting assembly comprises at least two limiting pins and at least two arc-shaped limiting grooves, wherein the at least two limiting pins are symmetrically disposed along the axial direction, and the at least two arc-shaped limiting grooves are symmetrically disposed along the axial direction.

* * * * *